US010188355B2

United States Patent
Giri et al.

(10) Patent No.: US 10,188,355 B2
(45) Date of Patent: Jan. 29, 2019

(54) BACKGROUND-SUPPRESSED, REDUCED FIELD-OF-VIEW RADIAL MAGNETIC RESONANCE IMAGING

(71) Applicants: Siemens Healthcare GmbH, Erlangen (DE); NorthShore University HealthSystem, Evanston, IL (US)

(72) Inventors: Shivraman Giri, Chicago, IL (US); Robert R. Edelman, Highland Park, IL (US); Ioannis Koktzoglou, Des Plaines, IL (US)

(73) Assignees: Siemens Healthcare GmbH, Erlangen (DE); Northshore University Healthsystem, Evanston, IL (US)

( * ) Notice: Subject to any disclaimer, the term of this patent is extended or adjusted under 35 U.S.C. 154(b) by 310 days.

(21) Appl. No.: 15/065,042

(22) Filed: Mar. 9, 2016

(65) Prior Publication Data
US 2017/0261581 A1    Sep. 14, 2017

(51) Int. Cl.
*A61B 5/00* (2006.01)
*A61B 5/055* (2006.01)
*G01R 33/3875* (2006.01)
*G01R 33/48* (2006.01)
(Continued)

(52) U.S. Cl.
CPC ............ *A61B 5/748* (2013.01); *A61B 5/0013* (2013.01); *A61B 5/055* (2013.01); *A61B 5/7203* (2013.01); *A61B 5/742* (2013.01); *G01R 33/3875* (2013.01); *G01R 33/4824* (2013.01); *G01R 33/4826* (2013.01); *G01R 33/4838* (2013.01);
(Continued)

(58) Field of Classification Search
None
See application file for complete search history.

(56) References Cited

U.S. PATENT DOCUMENTS

2008/0161678 A1\*  7/2008  Miyazaki ............ A61B 5/0263
                                                          600/419
2011/0228998 A1\*  9/2011  Vaidya ................ G01R 33/543
                                                          382/131
(Continued)

OTHER PUBLICATIONS

Feinberg D.A., Hoeninnger J.C., Crooks L.E., Kaufman L., Watts J.C., Arakawa M.,"Inner volume MR imaging: technical concepts and their application"; Radiology 156, 743-747.

*Primary Examiner* — Patrick Assouad
*Assistant Examiner* — Demetrius R Pretlow

(57) ABSTRACT

Embodiments relate to a method and system to improve fat suppression and reduce motion and off-resonance artifacts in magnetic resonance imaging (MRI) by using a background-suppressed, reduced field-of-view (FOV) radial imaging. The reduction of such artifacts provides improved diagnostic image quality, higher throughput of MRI scans for the imaging center, and increased patient comfort. By using a small FOV radial acquisition that only encompasses the structures of interest, structures that cause motion artifacts, such as the anterior abdominal wall, bowel loops, or blood vessels with pulsatile flow, are excluded from the image. According to an embodiment, combining a small FOV radial acquisition with one or more background-suppression techniques minimizes the impact of artifacts caused by anatomy outside of the FOV.

12 Claims, 6 Drawing Sheets

(51) Int. Cl.
   *G01R 33/483*   (2006.01)
   *G01R 33/56*   (2006.01)
(52) U.S. Cl.
   CPC ..... *G01R 33/5602* (2013.01); *G01R 33/5607* (2013.01); *A61B 2576/00* (2013.01)

(56) References Cited

U.S. PATENT DOCUMENTS

| | | | | |
|---|---|---|---|---|
| 2013/0006098 A1* | 1/2013 | Schmitt | .............. | G01R 33/4824 600/419 |
| 2013/0231409 A1* | 9/2013 | Fukuzawa | .............. | C08J 9/0061 521/58 |
| 2014/0200435 A1* | 7/2014 | Edelman | ................ | A61B 5/055 600/410 |
| 2015/0301140 A1* | 10/2015 | Lee | .................... | G01R 33/5602 324/309 |
| 2016/0081578 A1* | 3/2016 | Gazit | ..................... | A61B 5/055 600/410 |
| 2017/0131377 A1* | 5/2017 | Kim | ....................... | G01R 33/56 |
| 2017/0307715 A1* | 10/2017 | Eggers | ............... | G01R 33/4828 |

* cited by examiner

BACKGROUND-SUPPRESSED, REDUCED FIELD-OF-VIEW RADIAL MAGNETIC RESONANCE IMAGING

TECHNOLOGY FIELD

The present invention relates generally to acquisition of magnetic resonance images, and more particularly to utilizing a background-suppressed, reduced field-of-view in radial magnetic resonance imaging.

BACKGROUND

Magnetic resonance imaging (MRI) measures tissue-specific responses to a radio frequency (RF) stimulus in a strong static main magnetic field (BO). Specifically, the magnetization of tissue is aligned with BO. An initial RF pulse tips the magnetization out of this alignment and rotates with a tissue-specific RF frequency, resulting in a signal that is picked up with a receiver coil. Additional magnetic field gradient pulses (G) are used to spatially encode the RF signal that in turn is used to construct an image.

Before acquiring images, the MR scanner goes through an adjustment step, whereby the transmitter frequency is appropriately tuned so as to stimulate only desired tissue, excluding undesired signal from fat. If fat signal dominates in the field-of-view (FOV), as might happen in obese subjects with large amounts of subcutaneous fat, the scanner may not be appropriately tuned, thereby degrading the image quality.

MRI relies on a very homogeneous static magnetic field. Unfortunately, the magnetic field homogeneity of a clinical MRI scanner is degraded in the presence of the human body. In addition, static magnetic field homogeneity is degraded by interfaces between tissues of differing magnetic susceptibility (e.g., lung and liver), with this effect being highly patient dependent. Although the static magnetic field homogeneity can be improved by the process of shimming, the need to shim over a large FOV limits the efficacy of this technique. In addition to the reliance on static magnetic field homogeneity, MRI also requires that there is negligible motion from the time of the initial RF pulse through the application of gradient pulses and the reception of signal; this is because motion disrupts the spatial encoding introduced by the gradients, resulting in artifacts in the final images.

Image quality in MRI is affected not only by motion of the organ of interest, but also the motion of other organs within the FOV. For example, while imaging the thoracic spine, which is stationary, cardiac and breathing motion can degrade image quality in the spine region. Currently, MR images are generally acquired such that the FOV is large enough to cover all tissues within the slice of interest. In some attempts to reduce the FOV, efforts have focused on specially designed RF pulses to excite a small FOV covering the region of interest.

This document describes a method and system for minimizing artifacts from features in the slice that are outside of the region of interest.

SUMMARY

Embodiments of the present invention provide a method and system for magnetic resonance image acquisition utilizing a reduced field-of-view (FOV) in radial imaging techniques.

In an embodiment, a computer-implemented magnetic resonance imaging (MRI) method for acquiring images of a patient comprises: receiving, by an input processor, an indication of a field of view (FOV) that encompasses only an anatomy of interest of the patient, where the anatomy of interest is smaller than a full dimension of the patient; shimming, by a processor configured to communicate with the input processor, on the anatomy of interest within the FOV; applying, by the processor, radial imaging techniques on the shimmed FOV to acquire images of the anatomy; and generating, at a display processor configured to communicate with the processor, data representing the acquired images of the anatomy.

In an embodiment, a magnetic resonance imaging (MM) system for acquiring images of a patient comprises: a plurality of imaging coils comprising a plurality of gradient coils and a plurality of radio-frequency (RF) coils; and one or more processors configured to perform an imaging scan using the plurality of imaging coils, comprising: receiving an indication of a field of view (FOV) that encompasses only an anatomy of interest of the patient, where the anatomy of interest is smaller than a full dimension of the patient; shimming on the anatomy of interest within the FOV; and applying radial imaging techniques on the shimmed FOV to acquire the images of the anatomy. The system further comprises a display processor configured to communicate with the one or more processors to generate data representing the acquired images of the anatomy.

According to an embodiment, the radial imaging techniques comprise one or more magnetization preparation pulses to suppress unwanted features. The one or more magnetization preparation pulses may comprise at least one of (i) a regional saturation pulse that suppresses signal from specific regions pre-selected by a user; (ii) a fat-suppression pulse that suppresses signal from fat tissue; (iii) an in-plane saturation pulse that suppresses signal from all tissues in a slice; and (iv) intersecting inversion pulses that suppress signal in regions of the FOV that lie outside of their intersection.

In an embodiment, the radial imaging techniques comprise a radial quiescent-interval slice-selective (QISS) pulse sequence including a single magnetization preparation pulse.

According to an additional embodiment, the radial imaging techniques comprise one of two-dimensional and three-dimensional radial acquisition techniques.

The FOV, in an embodiment, is a reduced FOV compared to a required FOV for Cartesian acquisition.

In an embodiment, scan time for the radial imaging techniques is a reduced scan time compared to a required scan time for Cartesian acquisition.

According to an embodiment, the FOV excludes structures that cause motion artifacts.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

Embodiments of the present invention relate to a method and system to improve fat suppression and reduce motion and off-resonance artifacts in magnetic resonance imaging (MRI) by using a background-suppressed, reduced field-of-view (FOV) radial imaging. The reduction of such artifacts provides improved diagnostic image quality, higher throughput of MRI scans for the imaging center, and increased patient comfort.

Figure 1:
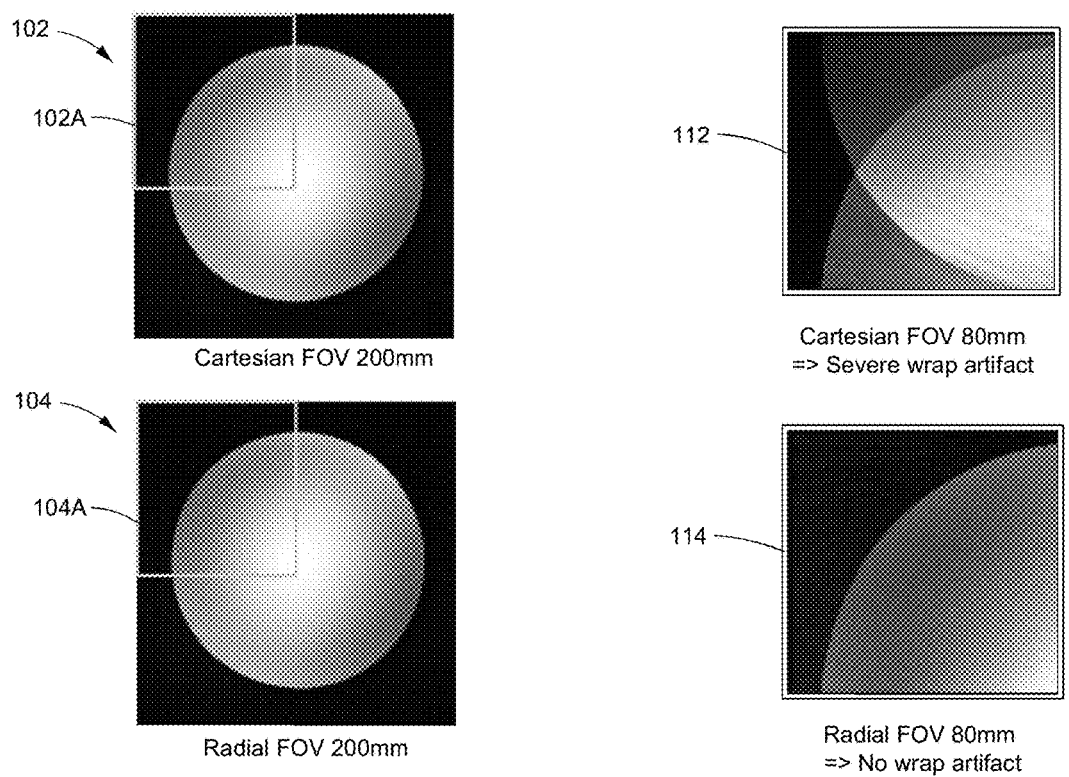
FIG. 1 is a diagram illustrating effects of a reduced field-of-view, utilized in accordance with embodiments described herein.

FIG. 1 is a diagram 100 illustrating effects of reducing the FOV with Cartesian acquisition (102, 112) and radial acquisition (104, 114). Boxes 102a and 104a represent the FOV used for the acquisition in 102 and 104, respectively. As seen in the reduced FOV 112 acquired with Cartesian k-space sampling, the features not covered within the FOV are wrapped around in the image, substantially degrading display of the imaged object. As seen in the reduced FOV 114 with radial k-space sampling, the features not covered within the FOV are benignly smeared throughout the image, without degrading the display of the object being imaged.

According to embodiments, off resonance artifacts are minimized by using a small field-of-view radial acquisition. In this case, shimming is only performed over the structures (i.e., the anatomy) of interest, giving a more homogeneous static magnetic field over desired structures, whereas structures that degrade static field homogeneity, such as air-containing bowel loops, lung tissue, large collections of fat, etc., are excluded.

The reduced FOV radial acquisition ensures that the frequency adjustment is correctly performed to the water peak, and not, for example, inadvertently to the fat peak in patients with large amounts of subcutaneous fat.

According to embodiments, 2D or 3D radial acquisition techniques may be utilized.

Embodiments disclosed herein may be suited to, but are not limited to, applications that entail a magnetization preparation pulse to suppress unwanted features in the image. Some of these preparations may include, but are not limited to:

1. a regional saturation pulse that suppresses signal from specific regions pre-selected by the user;
2. a fat-suppression pulse that suppresses signal from fat tissue;
3. an in-plane saturation pulse that suppresses signal from all tissues in a slice (used, for example, in angiography applications to accentuate the signal from inflowing blood compared with suppressed background); and
4. intersecting inversion pulses that suppress signal in regions of the FOV that lie outside of their intersection.

By using a small FOV radial acquisition that only encompasses the structures of interest, structures that cause motion artifacts, such as the anterior abdominal wall, bowel loops, or blood vessels with pulsatile flow, are excluded from the image. According to an embodiment, combining a small FOV radial acquisition with one or more of the above-identified background-suppression techniques minimizes the impact of artifacts caused by tissues outside of the FOV.

Figure 2A:
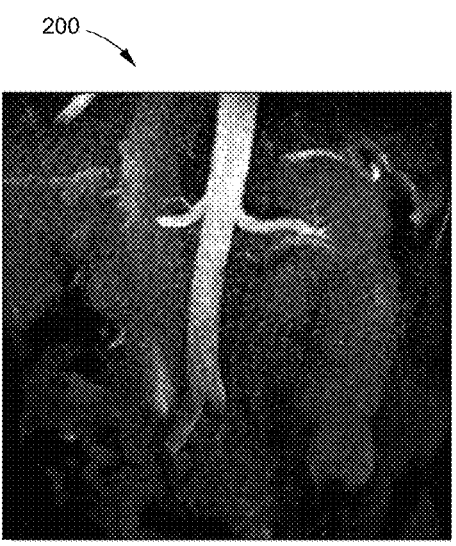
FIGS. 2A and 2B are diagrams illustrating MR images resulting from imaging techniques described herein, according to embodiments provided herein.

FIG. 2A illustrates the resulting application of the technique, according to embodiments disclosed herein, in an angiographic application in the abdomen for renal arteries. Conventional techniques use Cartesian acquisition, requiring large FOVs and long scan times in order to compensate for respiratory motion. Background-suppressed, reduced FOV radial imaging, according to embodiments disclosed herein, is accomplished with a single breath-hold during which the entire vascular tree of interest is imaged without degradation from bowel-loop motion or static magnetic field inhomogeneity caused by bowel gas, as seen in the resulting MR image 200.

Figure 2B:

FIG. 2B illustrates the resulting application of the disclosed method of background-suppressed, reduced FOV radial imaging on the heart. Resulting MR image 250 is a dark blood cardiac morphological image using small FOV radial imaging.

Figure 3A:
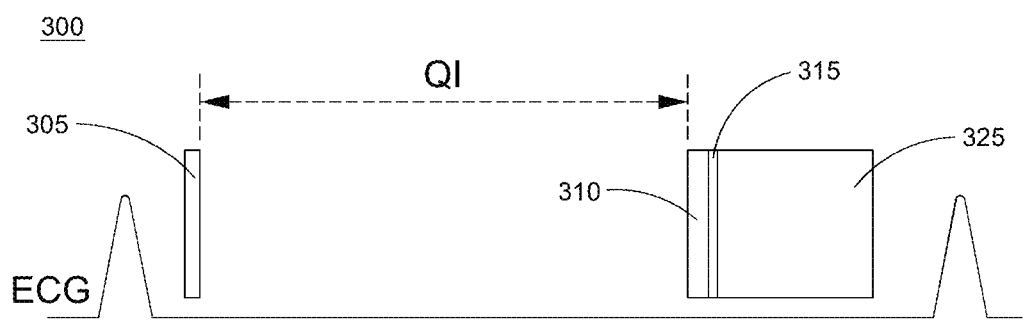
FIG. 3A is a diagram illustrating an exemplary pulse sequence utilized with the imaging techniques described herein.
Figure 3B:
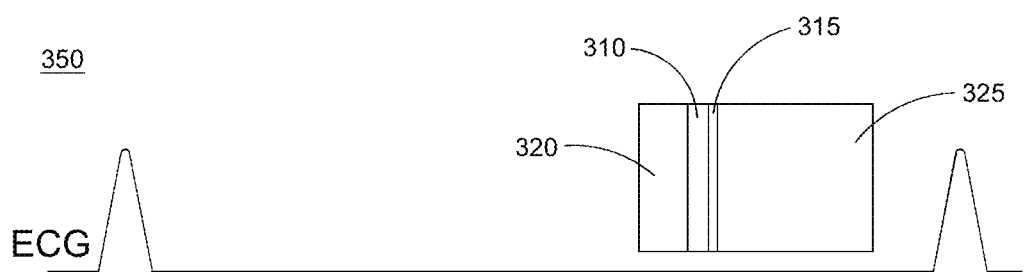
FIG. 3B is a comparison pulse sequence, according to embodiments provided herein.

FIG. 3A is a diagram illustrating an exemplary pulse sequence utilized with the imaging techniques described herein, according to embodiments provided herein. FIG. 3A is a representation of an exemplary radial quiescent-interval slice-selective (QISS) pulse sequence 300; and FIG. 3B is a representation of an exemplary 2D T2-prepared balanced steady-state free-precession (bSSFP) pulse sequence 350. 305 represents an in-plane inversion pulse (a magnetization preparation pulse); 310 a fat saturation pulse; 315 a bSSFP alpha/2 ramp pulse; 320 a T2 preparation pulse; and 325 a radial bSSFP readout. As shown in FIGS. 3A and 3B, the QISS pulse sequence 300 involves the application of a single magnetization preparation pulse (pulse 305); whereas the T2-prepared bSSFP pulse sequence 350 applies four RF pulses during the magnetization preparation, resulting in a substantial increase in SAR.

The fat saturation pulse 310 is an example of a background suppression pulse that selectively suppresses signal from fat. The bSSFP alpha/2 ramp pulse 315 helps to stabilize the signal from the bSSFP readout. The T2 preparation pulse 320 is an effective background suppression pulse (suppresses background muscle signal so that arteries are accentuated in comparison).

Radial QISS is immune from fold over artifacts, which allows the use of much smaller FOV than is practical using Cartesian imaging. With radial QISS, the high degree of background suppression from the combination of in-plane tissue inversion and fat suppression minimizes streak artifacts, which facilitates the use of high under-sampling factors.

As an example, for Cartesian QISS, a matrix size of 256×170, FOV of 358-mm×237-mm, parallel acceleration (ipat) factor of 2 was necessary to obtain the MR anatomy of interest. In contrast, for radial QISS, the matrix of 160 and FOV of 225-mm squared is sufficient.

According to embodiments disclosed herein, scan time is reduced when utilizing small FOV radial acquisition. On most modern MRI systems, Cartesian and radial trajectories typically support under-sampling factors of 2 and 5, respectively. As an example, when imaging the coronary arteries with 1 mm spatial resolution and 80 ms temporal resolution using a cardiac-gated MRI sequence with 4 ms repetition time, a Cartesian MRI scan acquiring a 320 mm square field of view would require (320 mm/1 mm)/(80 ms/4 ms)*(½)=8 heartbeats to complete. With the method described herein (i.e., small FOV radial acquisition), assuming that a smaller 160 mm square field of view is used due to the lack of fold-over and streak artifacts, the scan only requires (160 mm/1 mm)*pi/2/(80 ms/4 ms)*(⅕)=2.5 heartbeats to complete.

For imaging the abdominal organs such as liver, kidneys, and prostate, background suppressed, reduced FOV radial imaging, according to embodiments disclosed herein, can be used to minimize the impact of: motion from such sources as bowel loops, pulsatile blood flow, and anterior abdominal wall; and off-resonance effects caused by air in bowel loop and lungs.

In the heart, the reduced radial FOV, according to embodiments disclosed herein, is beneficial in improving the quality of fat suppression and avoiding off-resonance effects when a balanced steady-state precession pulse sequence is used to collect the data.

In angiographic applications, most structures need to be suppressed, except vascular blood. Depending on the vascular branch being imaged, background-suppressed, reduced FOV radial imaging, according to embodiments disclosed herein, can be used to minimize motion artifacts from moving organs as well as undesired signal from subcutaneous fat.

For imaging of the thoracic and lumbar spine, a background-suppressed, reduced FOV radial turbo spin-echo pulse sequence can be used to image the vertebral column and spinal cord while excluding the contents of the thorax and abdomen, respectively. In the cervical spine, the FOV can be reduced to exclude swallowing artifacts from the mouth and pharynx.

Figure 4:
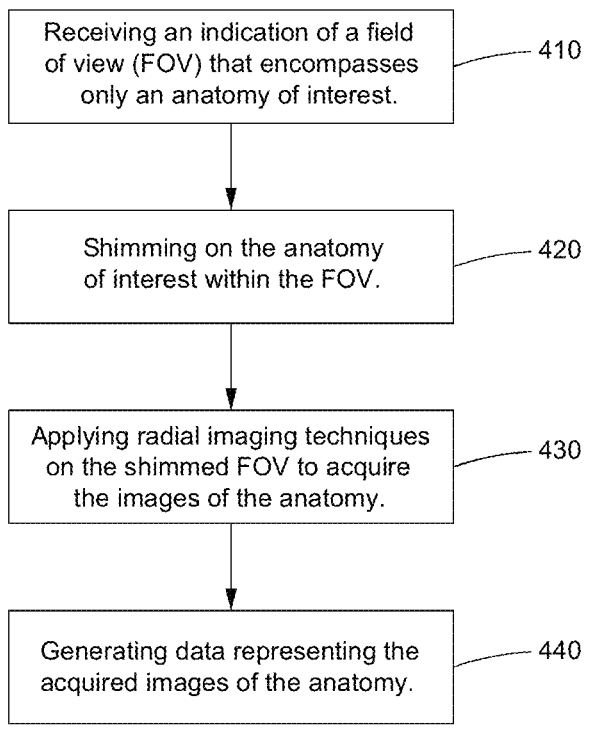
FIG. 4 is a flowchart illustrating a computer-implemented MRI method for acquiring images of an anatomy of a patient, according to embodiments provided herein.

FIG. 4 is a flowchart 400 illustrating a computer-implemented MRI method for acquiring images of an anatomy of a patient, according to embodiments provided herein. At 410, an indication of a FOV that encompasses only an anatomy of interest of the patient is received by an input processor. According to embodiments herein, the anatomy of interest is smaller than a full dimension of the patient. The FOV and the anatomy of interest may be determined by a user and inputted into a MRI system, such as system 500 described below with reference to FIG. 5.

At 420, shimming on the anatomy of interest within the FOV is performed by a processor configured to communicate with the input processor. As described above, the shimming provides a more homogeneous static magnetic field over desired structures (i.e., the anatomy of interest).

At 430, radial imaging techniques are applied by the processor on the shimmed FOV to acquire the images of the anatomy. Imaging can be done during free-breathing or with the patient holding their breath. As described above, various background-suppression pulses may be applied prior to radial imaging.

At 440, data representing the acquired images of the anatomy is generated at a display processor configured to communicate with the processor. The data may include images such as those shown in FIGS. 2A and 2B.

Figure 5:
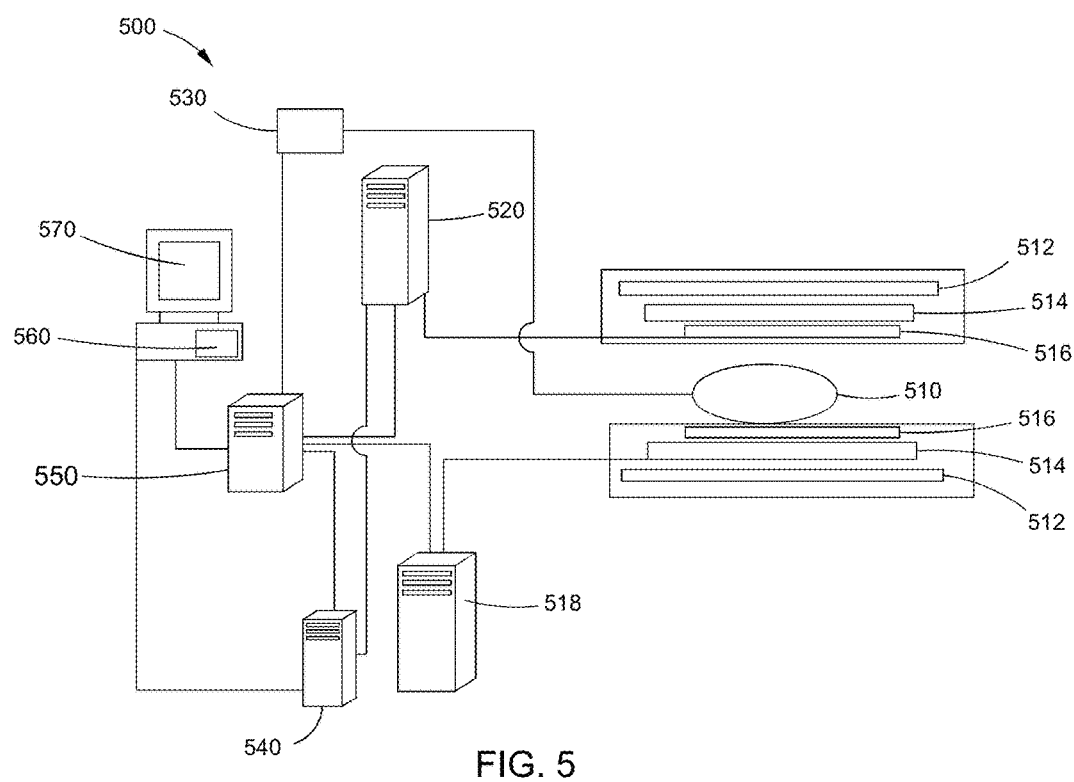
FIG. 5 illustrates a MRI system for acquiring images of an anatomy of a patient, according to embodiments provided herein.

Turning to FIG. 5, a system 500 for acquiring MRI images of an anatomy of a patient, according to embodiments provided herein, is illustrated. The system 500 includes a source 510 of the tissue, such as a patient. 512, 514, and 516 represent the coils and magnets of an MRI system and are, in an exemplary embodiment, a high field magnet 512, a gradient coil 514, and a radio-frequency (RF) coil 516. Processors 518 (gradient and shim coil controller) and 520 (radio-frequency controller) control the MR magnets and coils. The MRI system components 512, 514, and 516 and processors 518 and 520 depicted in FIG. 5 are one example of an MRI system; other components and processors may be used as known to one of skill in the art to obtain an MR image of tissue.

The system 500 further includes an input processor 530, an image data processor 540, a display processor 560, and an interface 570. A central control system 550 controls the overall operation of and data communication between each of the processors 518, 520, 530, 540, and 560.

Figure 6:
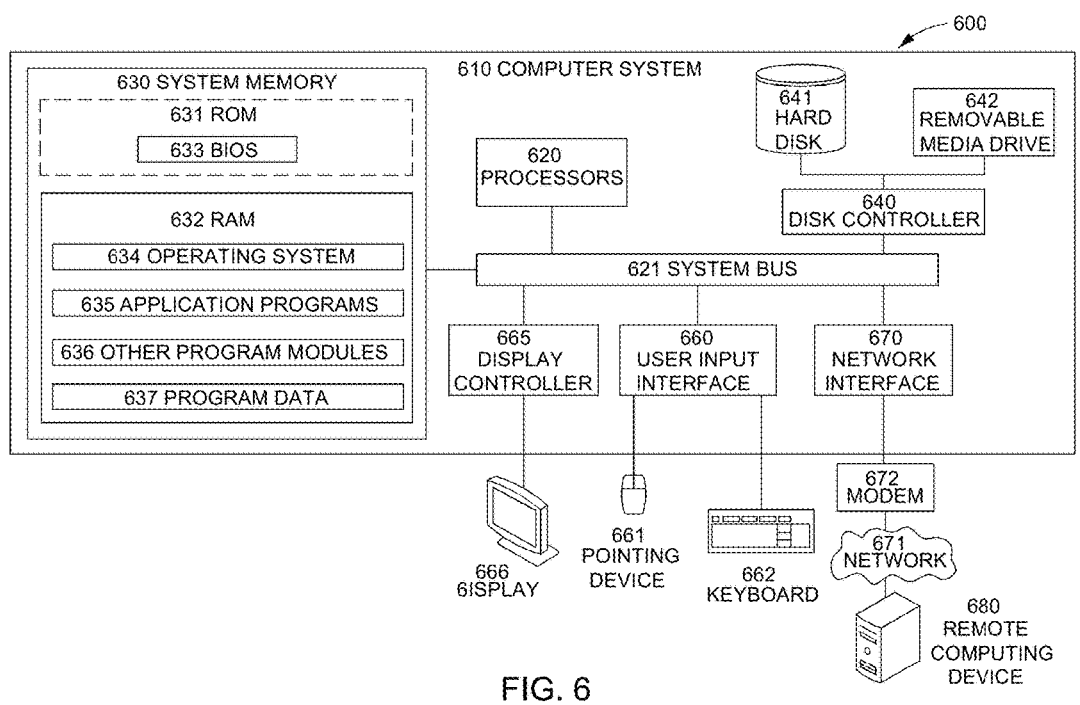
FIG. 6 is an exemplary computing environment in which embodiments disclosed herein may be implemented.

FIG. 6 illustrates an exemplary computing environment 600 within which embodiments of the invention may be implemented. Computing environment 600 may include computer system 610, which is one example of a computing system upon which embodiments of the invention may be implemented. Computers and computing environments, such as computer 610 and computing environment 600, are known to those of skill in the art and thus are described briefly here.

As shown in FIG. 6, the computer system 610 may include a communication mechanism such as a bus 621 or other communication mechanism for communicating information within the computer system 610. The system 610 further includes one or more processors 620 coupled with the bus 621 for processing the information. The processors 620 may include one or more central processing units (CPUs), graphical processing units (GPUs), or any other processor known in the art.

The computer system 610 also includes a system memory 630 coupled to the bus 621 for storing information and instructions to be executed by processors 620. The system memory 630 may include computer readable storage media in the form of volatile and/or nonvolatile memory, such as read only memory (ROM) 631 and/or random access memory (RAM) 632. The system memory RAM 632 may include other dynamic storage device(s) (e.g., dynamic RAM, static RAM, and synchronous DRAM). The system memory ROM 631 may include other static storage device (s) (e.g., programmable ROM, erasable PROM, and electrically erasable PROM). In addition, the system memory 630 may be used for storing temporary variables or other intermediate information during the execution of instructions by the processors 620. A basic input/output system 633 (BIOS) containing the basic routines that help to transfer information between elements within computer system 610, such as during start-up, may be stored in ROM 631. RAM 632 may contain data and/or program modules that are immediately accessible to and/or presently being operated on by the processors 620. System memory 630 may additionally include, for example, operating system 634, application programs 635, other program modules 636 and program data 637.

The computer system 610 also includes a disk controller 640 coupled to the bus 621 to control one or more storage devices for storing information and instructions, such as a magnetic hard disk 641 and a removable media drive 642 (e.g., floppy disk drive, compact disc drive, tape drive, and/or solid state drive). The storage devices may be added to the computer system 610 using an appropriate device interface (e.g., a small computer system interface (SCSI), integrated device electronics (IDE), Universal Serial Bus (USB), or FireWire).

The computer system 610 may also include a display controller 665 coupled to the bus 621 to control a display or monitor 666, such as a cathode ray tube (CRT) or liquid crystal display (LCD), for displaying information to a computer user. The computer system 610 includes an input interface 660 and one or more input devices, such as a keyboard 662 and a pointing device 861, for interacting with a computer user and providing information to the processors 620. The pointing device 661, for example, may be a mouse, a trackball, or a pointing stick for communicating direction information and command selections to the processors 620 and for controlling cursor movement on the display 666. The display 666 may provide a touch screen interface which allows input to supplement or replace the communication of direction information and command selections by the pointing device 661.

The computer system 610 may perform a portion or all of the processing steps of embodiments of the invention in response to the processors 620 executing one or more sequences of one or more instructions contained in a memory, such as the system memory 630. Such instructions may be read into the system memory 630 from another computer readable medium, such as a hard disk 641 or a removable media drive 842. The hard disk 641 may contain one or more datastores and data files used by embodiments of the present invention. Datastore contents and data files may be encrypted to improve security. The processors 620 may also be employed in a multi-processing arrangement to execute the one or more sequences of instructions contained in system memory 630. In alternative embodiments, hard-wired circuitry may be used in place of or in combination with software instructions. Thus, embodiments are not limited to any specific combination of hardware circuitry and software.

As stated above, the computer system 610 may include at least one computer readable medium or memory for holding instructions programmed according to embodiments provided herein and for containing data structures, tables, records, or other data described herein. The term "computer readable medium" as used herein refers to any medium that participates in providing instructions to the processors 620 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 641 or removable media drive 642. Non-limiting examples of volatile media include dynamic memory, such as system memory 630. Non-limiting examples of transmission media include coaxial cables, copper wire, and fiber optics, including the wires that make up the bus 621. Transmission media may also take the form of acoustic or light waves, such as those generated during radio wave and infrared data communications.

The computing environment 600 may further include the computer system 610 operating in a networked environment using logical connections to one or more remote computers, such as remote computer 680. Remote computer 680 may be a personal computer (laptop or desktop), a mobile device, a server, a router, a network PC, a peer device or other common network node, and typically includes many or all of the elements described above relative to computer system 610. When used in a networking environment, computer system 610 may include modem 672 for establishing communications over a network 671, such as the Internet. Modem 672 may be connected to system bus 621 via user network interface 670, or via another appropriate mechanism.

Network 671 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 610 and other computers (e.g., remote computing system 680). The network 671 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 671.

As described herein, the various systems, subsystems, agents, managers and processes can be implemented using hardware components, software components and/or combinations thereof.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A computer-implemented magnetic resonance imaging (MRI) method for acquiring images of a patient, the method comprising:
    receiving, by an input processor, user input comprising an indication of a field of view (FOV) that encompasses only an anatomy of interest of the patient, the anatomy of interest smaller than a full dimension of the patient;
    shimming, by a processor configured to communicate with the input processor, on the anatomy of interest within the FOV;
    applying, by the processor, a radial quiescent-interval slice-selective (QISS) pulse sequence including a magnetization preparation pulse to the shimmed FOV to acquire images of the anatomy of interest; and
    generating, at a display processor configured to communicate with the processor, data representing the acquired images of the anatomy of interest.

2. The method of claim 1, wherein the magnetization preparation pulse comprises at least one of (i) a regional saturation pulse that suppresses signal from specific regions pre-selected by a user; (ii) a fat-suppression pulse that suppresses signal from fat tissue; (iii) an in-plane saturation pulse that suppresses signal from all tissues in a slice; and (iv) intersecting inversion pulses that suppress signal in regions of the FOV that lie outside of their intersection.

3. The method of claim 1, wherein the radial imaging techniques comprise one of two-dimensional and three-dimensional radial acquisition techniques.

4. The method of claim 1, wherein the FOV is a reduced FOV compared to a Cartesian acquisition FOV.

5. The method of claim 1, wherein scan time for the radial imaging techniques is a reduced scan time compared to a required scan time for Cartesian acquisition.

6. The method of claim 1, wherein the FOV excludes structures that cause motion artifacts.

7. A magnetic resonance imaging (MRI) system for acquiring images of a patient, the system comprising:
    a plurality of imaging coils comprising:

a plurality of gradient coils;
a plurality of radio-frequency (RF) coils;
one or more processors configured to perform an imaging scan using the plurality of imaging coils, comprising:
receiving user input comprising an indication of a field of view (FOV) that encompasses only an anatomy of interest of the patient, the anatomy of interest smaller than a full dimension of the patient;
shimming on the anatomy of interest within the FOV;
applying a radial quiescent-interval slice-selective (QISS) pulse sequence including a magnetization preparation pulse to the shimmed FOV to acquire images of the anatomy of interest; and
a display processor configured to communicate with the one or more processors to generate data representing the acquired images of the anatomy of interest.

8. The system of claim 7, wherein the magnetization preparation pulse comprises at least one of (i) a regional saturation pulse that suppresses signal from specific regions pre-selected by a user; (ii) a fat-suppression pulse that suppresses signal from fat tissue; (iii) an in-plane saturation pulse that suppresses signal from all tissues in a slice; and (iv) intersecting inversion pulses that suppress signal in regions of the FOV that lie outside of their intersection.

9. The system of claim 7, wherein the radial imaging techniques comprise one of two-dimensional and three-dimensional radial acquisition techniques.

10. The system of claim 7, wherein the FOV is a reduced FOV compared to a Cartesian acquisition FOV.

11. The system of claim 7, wherein scan time for the radial imaging techniques is a reduced scan time compared to a required scan time for Cartesian acquisition.

12. The system of claim 7, wherein the FOV excludes structures that cause motion artifacts.

* * * * *